United States Patent [19]
Young et al.

[11] Patent Number: 5,337,746
[45] Date of Patent: Aug. 16, 1994

[54] "IN-VIVO" OXYGEN TENSION MEASUREMENT

[76] Inventors: Howard L. Young, 56 Cheriton Drive, Thornhill, Cardiff CF4 9DF; Richard H. Lowndes, 12 Landsdowne Road, Newport, Gwent NP9 3FZ, both of Great Britain

[21] Appl. No.: 651,236

[22] PCT Filed: Aug. 9, 1989

[86] PCT No.: PCT/GB89/00908

§ 371 Date: Mar. 21, 1991

§ 102(e) Date: Mar. 21, 1991

[87] PCT Pub. No.: WO90/01292

PCT Pub. Date: Feb. 22, 1990

[30] Foreign Application Priority Data

Aug. 11, 1988 [GB] United Kingdom .......... 8819086.3

[51] Int. Cl.$^5$ ............................................. A61B 5/00
[52] U.S. Cl. ........................................ 128/635; 128/642
[58] Field of Search .......... 128/635, 642, 734, 736; 204/403, 415, 153.16, 153.17

[56] References Cited

U.S. PATENT DOCUMENTS

| | | | |
|---|---|---|---|
| 3,336,919 | 8/1967 | Russ | 128/635 |
| 3,504,664 | 4/1970 | Haddad | 128/635 |
| 4,334,541 | 6/1982 | Leist et al. | 128/632 |
| 4,534,355 | 8/1985 | Potter | 128/635 |
| 4,685,465 | 8/1987 | Klitgaard et al. | 128/635 |
| 4,805,122 | 2/1989 | McDavid et al. | 364/557 |
| 4,930,506 | 6/1990 | Ullrich | 128/633 |
| 4,995,391 | 2/1991 | Jensen et al. | 128/635 |

FOREIGN PATENT DOCUMENTS

| | | | |
|---|---|---|---|
| 3633016 | 4/1988 | Fed. Rep. of Germany | 128/635 |
| 2093190 | 8/1982 | United Kingdom | 128/635 |

Primary Examiner—Angela D. Sykes
Attorney, Agent, or Firm—Young & Thompson

[57] ABSTRACT

A sensor for use in detecting variable characteristics of a living body in vivo, comprises an electrode assembly designed to be introduced into the body and having an exposed electrode coupled to a detecting measuring circuit, and an electrical heater in proximity to and embedded in a synthetic plastic body of the electrode. The heater is alternatively operable to heat the electrode whilst in use as a sensor or to heat the plastic body to cure it during manufacture.

4 Claims, 4 Drawing Sheets

"IN-VIVO" OXYGEN TENSION MEASUREMENT

This invention relates to the measurement of oxygen tension or partial pressure in human or animal tissue in-vivo. It is well known that effective healing after surgical procedures depends largely on the oxygen partial pressure within the tissues and it is also known that this oxygen "tension" can be measured or detected by means of an electrode assembly coupled to an electrical circuit which provides an indication of the electrical potential between electrodes.

These measurements are particularly important, for example, in connection with colonic anastomotic leakage which is believed often to follow from inadequate blood supply and it is an object of the invention to provide improved apparatus and procedures for checking whether adequate levels of oxygen are available at different sites in the body tissues.

According to one aspect of this invention there is provided a sensor for use in detecting variable characteristics of a living body in-vivo, comprising an electrode assembly designed to be introduced into the body, and having at least one exposed electrode coupled to a detecting or measuring circuit, and means for warming the electrode in use, by means of an electrical heater in proximity to and embedded in a synthetic plastic body of the electrode assembly, and a thermistor or other temperature sensing device acting as an automatic temperature control, the same heater also being connectable with an alternative control circuit designed to raise the temperature of the heater well above routine warming temperatures so as to "cure" the body of plastic material during manufacture.

The sensor preferably includes special controls with safety devices to prevent the heater exceeding a dangerous temperature in normal use.

From another aspect the invention consists in a sensor for use in detecting variable characteristics of a living body in-vivo, comprising an electrode assembly designed to be introduced into the body, and having at least one exposed electrode coupled to a detecting or measuring circuit, and means for warming the electrode in use, by means of an electrical heater in proximity to the electrode and embedded in a synthetic plastic body, and a thermistor or other temperature sensing device acting as an automatic temperature control, the electrode being in the form of a thin walled tube embedded in the synthetic plastics material, with the heater and/or the thermal sensing element located on or closely adjacent to the tube.

Preferably the diameter of the tube is approximately half the diameter of the plastics body. This places the heater and temperature sensor at approximately equal distances from all points throughout the body.

The invention also consists in a method of detecting the condition of internal tissues in-vivo, by sensing the oxygen partial pressure, using an oxygen sensing electrode assembly coupled to an electrical detecting/measuring circuit, in which the measuring circuit is designed and/or adjusted to be responsive to any one or all of the following conditions:

a) an absolute oxygen partial pressure of 18-22 mm Hg
b) an oxygen partial pressure of between 40% and 60% of the base line reading (average) at the same site
c) an oxygen partial pressure of 35%-45% of the reading taken on the ileum
d) an arterial oxygen level of 12% to 17%.

For practising this procedure the invention also provides an electrical instrument for use in medical, surgical and clinical procedures, including an operating "head" designed for application to a part of the body in-vivo, and capable of being sterilised, means for connecting the head to a remote electrical detecting/measuring/recording/display device, which is not designed for sterilisation, and a portable control unit, designed for sterilisation, and having electrical connections to the head and to the remote device.

Preferably the arrangement is such as to allow the portable control unit to be located physically adjacent to the head.

The invention may be performed in various ways and one specific embodiment, with some possible modifications, will now be described by way of example, with reference to the accompanying drawings, in which.

Figure 1:
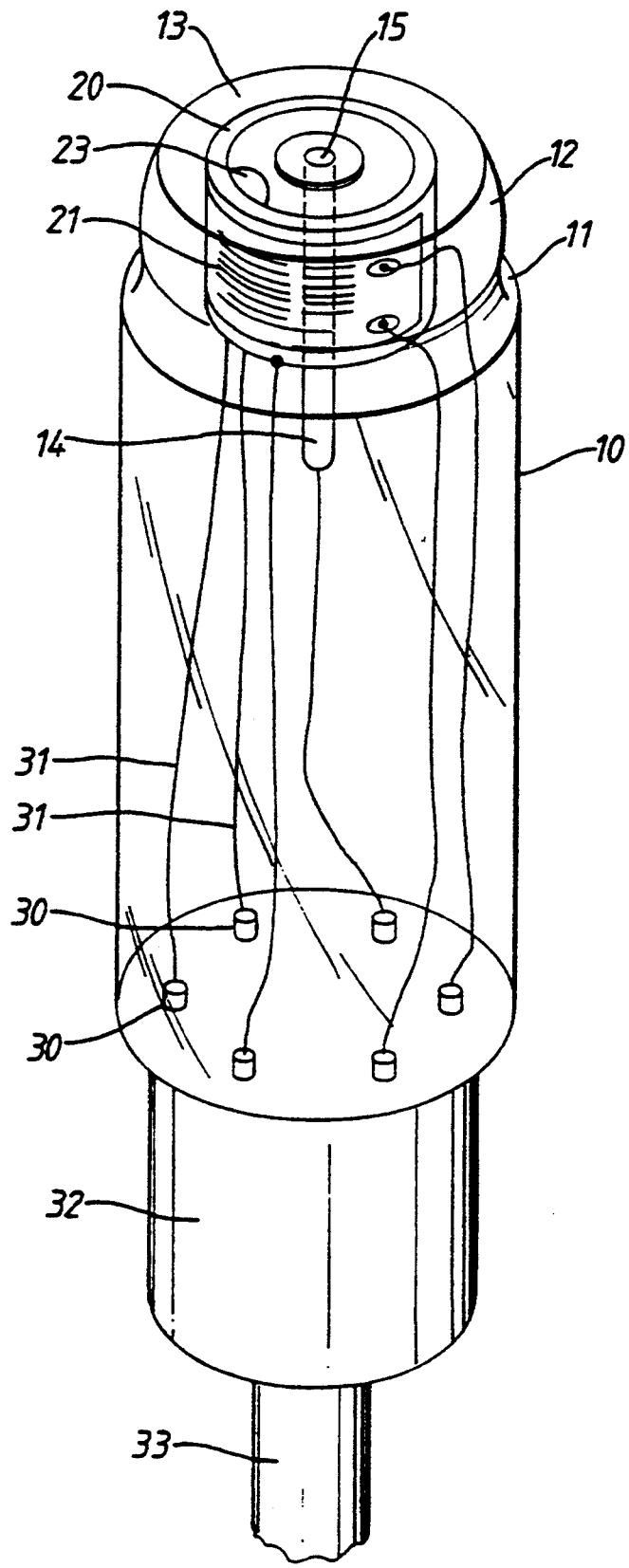
FIG. 1 is a diagrammatic perspective view of an electrode assembly head according to the invention.

The electrode heater illustrated in FIG. 1 comprises a body 10 formed of a synthetic plastics material such as an epoxy resin which is of a type that is thermally "cured" in manufacture. The body has a groove 11 near its upper end with a slightly enlarged rounded head 12 presenting a flat upper surface 13. Within the body is a central metal cathode 14 having its upper end 15 exposed on the surface 13. The anode may be formed of platinum. Surrounding this central cathode is an anode tube 20 formed of silver and co-axial with the cathode and of a diameter approximately half that of the body 10. Physically attached to this anode tube 20 is a small electrical heater 21 which is preferably of a type described in our co-pending British Application No. 8607378 (Specification No. 2173422). Also physically attached to the anode tube is a thermistor bead 23 designed to provide a temperature responsive control for the heater. The heater, thermistor, and the anode and cathode electrodes, are connected respectively to terminals 30 in the base of the electrode assembly by way of conductors 31 embedded in the plastic.

These conductors are led out through a sealed connector 32 to a flexible multi-core lead 33 and the design is such that the whole unit is entirely sealed and waterproof and resistant to temperature and is therefore capable of being sterilised for repeated use in clinical operations.

Figure 2:
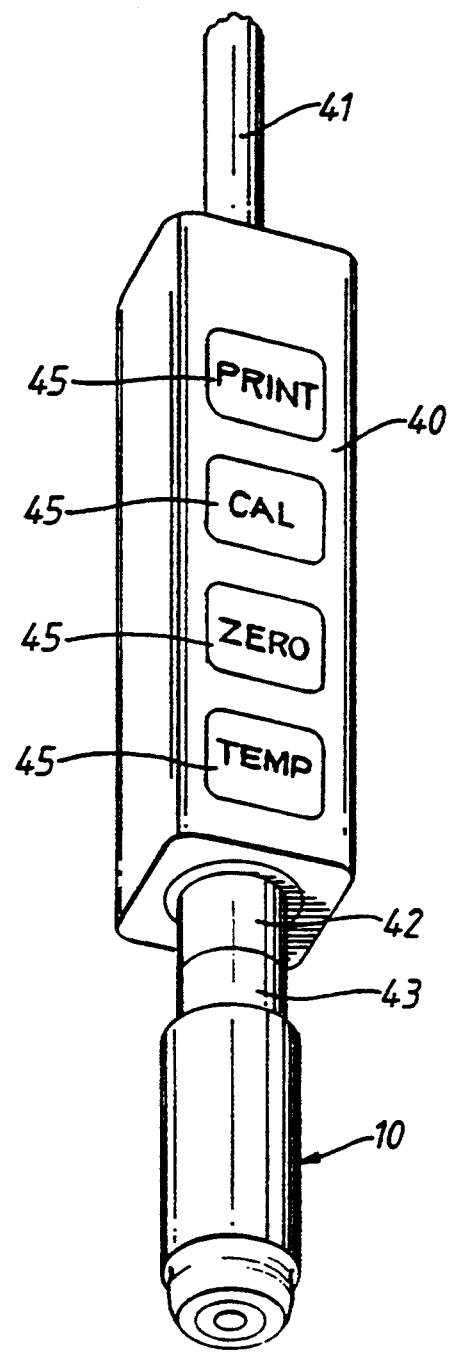
FIG. 2 is a perspective view of a detachable control unit for use therewith.

The device illustrated in FIG. 2 is a small control unit in the form of a "key-pad" 40 having a multi-core connector 41 by which it can be coupled to external electrical control and metering and supply circuits. The unit also has a coupling 42 for direct connection to the electrode assembly 10 via a plug-in sealed joint 43. The control unit is operated by sealed press buttons 45 and is therefore capable of being sterilised and re-used. The circuit connections between the press button and the metering unit and the electrode head allow the surgeon complete control of all electrical circuits and meters directly from the operating table and this greatly facilitates the necessary operations such as calibration, temperature control and metering.

Figure 3:
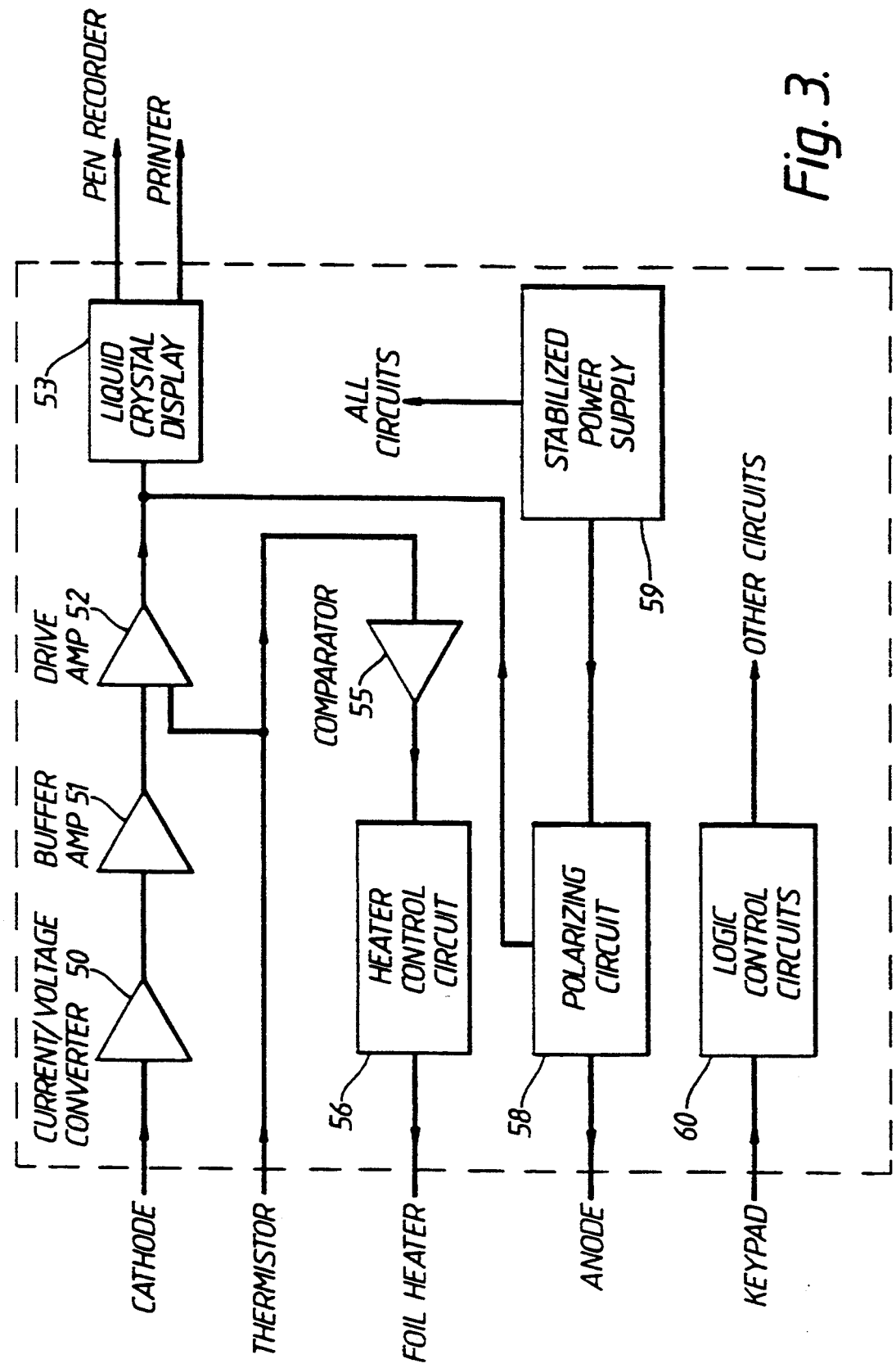
FIG. 3 is a circuit diagram illustrating the external electrical system and measuring circuits.

The circuit diagram of FIG. 3 illustrates diagrammatically the main components of the control circuit with numbered conductors 1 to 5 to be connected to the cathode 14, thermistor 23, heater 21, anode 20 and control unit 40. The cathode terminal leads through the current/voltage converter 50 and amplifier 51 to a drive amplifier 52 and thence to the display unit 53, from which further outputs may lead to a pen recorder and printer. The thermistor terminal has one input to the drive amplifier 52 and another input to the comparator 55 which leads through the heater control unit 56 to the heater terminal. The anode connection leads through the polarizing circuit 58 to the display 53 and is also connected to a stabilised power supply 59 arranged to supply all circuits. The portable control unit 40 is connected through various logic control circuits 60 to the other components of the total system.

Figure 4:
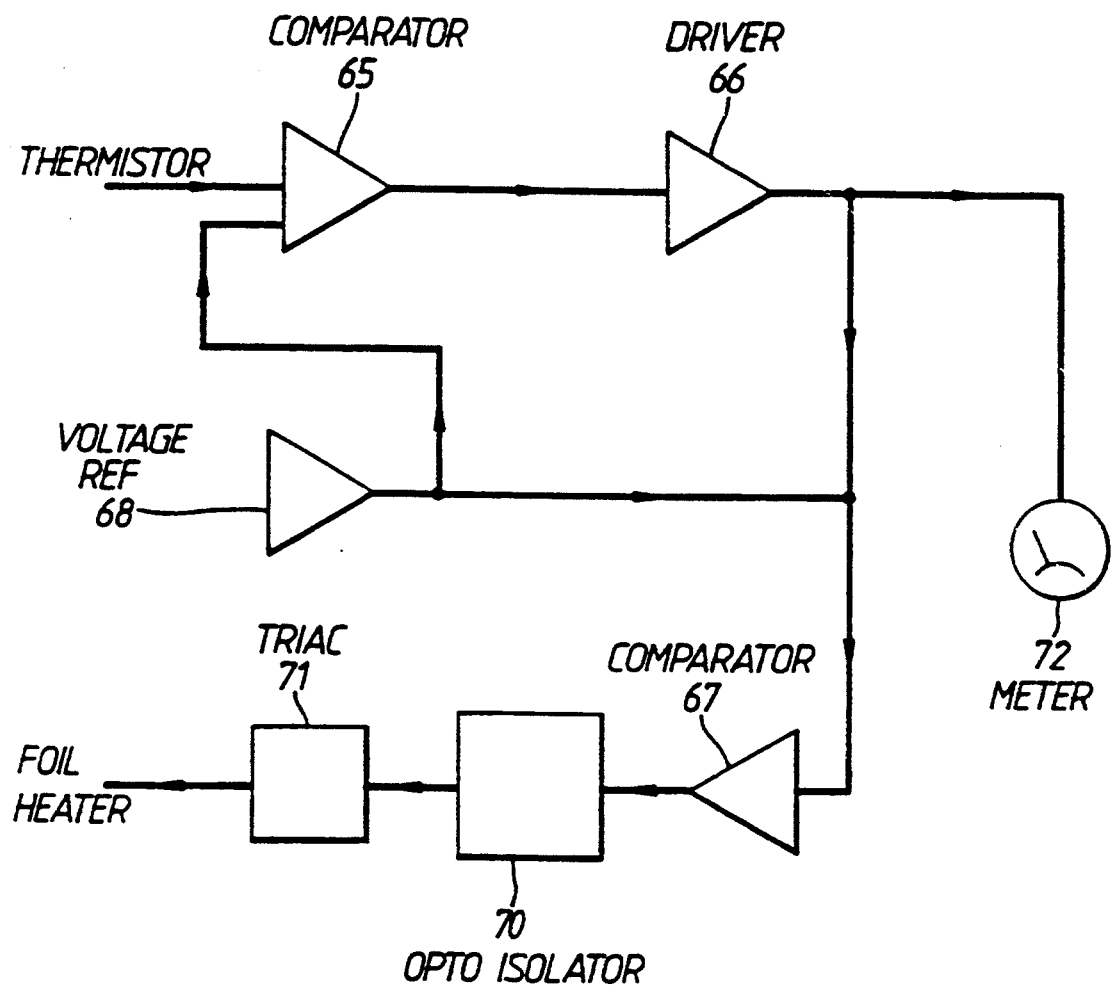
FIG. 4 is a circuit diagram illustrating an external heating circuit for use in manufacture of the head.

It will be appreciated that in manufacture the temperature of the heater needs to be raised to a comparatively high level of say 80° C. in order to cure the synthetic resin. It is vital however, that the temperature of the heater should not rise appreciably above body temperature when the electrode is in use. Accordingly an entirely separate control circuit is provided to energise and control the heater during the manufacturing process, and this is illustrated in FIG. 4. Here the thermistor is connected as one input to a comparator 65 having an output to a driver 66 whose output is fed to a second comparator 67. The voltage reference 68 has one input to the comparator 65 and is also connected to the second comparator 67 the output from which leaves via an opto-isolator 70 and a triac 71 to the foil heater 21. The circuit is monitored by a meter 72.

The apparatus also includes safety devices to ensure that the heater circuit will not accidentally allow the heater to exceed a safety level. Various different safety devices are possible and, for example, there may be an automatic interruptor switch in the heater circuit of FIG. 4 arranged to be actuated automatically when the electrode assembly is coupled to the control unit 40. Alternatively or in addition there may be alarm or warning devices actuated automatically when the heater circuit of FIG. 4 is energised.

In use the top surface 13 of the electrode head has a thin film of electrolyte applied and covered by a thin sheet of pervious membrane such as a synthetic plastics, which is held in place by a band located in the groove 11. For sterilising the band and sheet are removed.

We claim:

1. Apparatus for detecting the condition of internal tissues in-vivo, including an operating head comprising:
a sensor being capable of being sterilised,
means for connecting the head to a remote electrical detecting/measuring/recording/display device, and a portable control unit, designed for sterilisation, and having electrical connections to the head and to the remote device,
the sensor comprising an electrode assembly designed to be introduced into the body, and having at least one exposed electrode for connection to a detecting or measuring circuit, and means warming the electrode in use, by means of an electrical heater in proximity to and embedded in a synthetic plastic body of the electrode assembly, and a temperature sensing device acting as an automatic temperature control, characterised in that the body of plastic material is cured during manufacture of the sensor by connecting said heater to an alternative control circuit designed to raise the temperature of the heater well above routine warming temperature so as to "cure" the body of plastic material.

2. Apparatus according to claim 1 including means for coupling the portable control unit adjacent to the head.

3. An electrical instrument for detecting the condition of internal tissues in-vivo, by sensing the oxygen partial pressure, using an oxygen sensing electrode assembly coupled to an electrical detecting/measuring circuit, for use in medical, surgical and clinical procedures, including an operating "head" designed for application to apart of the body in-vivo, and capable of being sterilised, means for connecting the head to a remote electrical detecting/measuring/recording/display device, and a portable control unit, designed for sterilisation, and having electrical connections to the head and to the remote device.

4. An electrical instrument according to claim 3, including means for coupling the portable control unit adjacent to the head.

* * * * *